(12) United States Patent
Zribi et al.

(10) Patent No.: US 7,574,089 B1
(45) Date of Patent: Aug. 11, 2009

(54) OPTOFLUIDIC DEVICES AND METHODS OF USING THE SAME

(75) Inventors: Anis Zribi, Rexford, NY (US); Wei-Cheng Tian, Clifton Park, NY (US); Yuan-Hsiang Lee, Winchester, MA (US); Min-Yi Shih, Niskayuna, NY (US)

(73) Assignee: GE Homeland Protection, Inc., Newark, CA (US)

(*) Notice: Subject to any disclaimer, the term of this patent is extended or adjusted under 35 U.S.C. 154(b) by 0 days.

(21) Appl. No.: 11/400,947

(22) Filed: Apr. 10, 2006

(51) Int. Cl.
*G02B 6/00* (2006.01)
*G02B 6/02* (2006.01)
*G02B 6/10* (2006.01)

(52) U.S. Cl. .................. 385/129; 385/122; 385/123; 385/130; 385/131; 385/132

(58) Field of Classification Search ......... 385/129–132, 385/122, 123
See application file for complete search history.

(56) References Cited

U.S. PATENT DOCUMENTS

| | | | |
|---|---|---|---|
| 4,120,588 A * | 10/1978 | Chaum | 356/460 |
| 6,244,753 B1 * | 6/2001 | O'Connor et al. | 385/75 |
| 6,480,638 B1 * | 11/2002 | Adkins et al. | 385/12 |
| 7,283,243 B2 * | 10/2007 | Langford et al. | 356/439 |
| 2003/0063884 A1 * | 4/2003 | Smith et al. | 385/129 |
| 2003/0174992 A1 * | 9/2003 | Levene et al. | 385/129 |
| 2005/0134836 A1 * | 6/2005 | Paldus et al. | 356/73 |

* cited by examiner

*Primary Examiner*—Frank G Font
*Assistant Examiner*—Jerry Blevins
(74) *Attorney, Agent, or Firm*—Joseph J. Christian (57) ABSTRACT

An optofluidic device is provided. The device includes a cladding region having a first refractive index, and a channel defined by the cladding region such that the cladding region forms an inner surface or an interface of the channel. The channel is configured to house one or more of a liquid, a solid, a gas, a colloidal, or a suspension sample, wherein the sample has a second refractive index, where the channel is configured to guide radiation, and where the first refractive index is lower than the second refractive index.

26 Claims, 6 Drawing Sheets

OPTOFLUIDIC DEVICES AND METHODS OF USING THE SAME

BACKGROUND

The invention relates generally to an optofluidic system for analysis. More particularly, the invention relates to an optofluidic device employing one or more of solid, liquid, gas, colloidal, or suspension samples.

Optofluidic devices are now used very often in applications such as, research, sensing systems, detection systems, drug identification, and biological or chemical analyses. Typically, optofluidic devices include an optical waveguide having a low refractive index cladding and a sample core with liquid samples. In general, Teflon® or amorphous fluoro-polymer is employed as low refractive index cladding. It should be appreciated that for the light to be retains inside the waveguide, it is required that the refractive index of the cladding be lower than the refractive index of the core.

There exists a need for a suitable optofluidic device with performance improvement, such as signal enhancement. Also, there exists a need for suitable cladding for these optofluidic devices that are configured to house a sample in a liquid or a gas environment.

SUMMARY

Embodiments of the invention are directed to an optofluidic device having a cladding region and a channel defined by the cladding region, a system employing the optofluidic device, and a method of using the optofluidic device.

One exemplary embodiment of the invention is an optofluidic device. The optofluidic device includes a cladding region having a first refractive index, and a channel defined by the cladding region such that the cladding region forms an inner surface or interface of the channel. The channel is configured to house one or more of a solid, a liquid, a gas, a colloidal, or a suspension sample, where the sample has a second refractive index. The first refractive index is lower than the second refractive index. The channel is configured to guide radiation.

Another exemplary embodiment of the invention is an optofluidic system employing an optofluidic device for providing an optical interaction path between a beam and a liquid or a gas sample. The device includes a first refractive index region, and a second refractive index region configured to dispose one or more of a solid, a liquid, a gas, a colloidal, or a suspension sample therein. The first refractive index region surrounds the second refractive index region to define a space for interaction between the beam and the sample region. The first refractive index is greater than the second refractive index.

Another exemplary embodiment of the invention is an optofluidic device. The optofluidic device includes a cladding region having a first refractive index, and a channel defined by the cladding region such that the cladding region forms an inner surface or an interface of the channel. The channel is configured to house one or more of a solid, a liquid, a gas, a colloidal, or a suspension sample, where the sample has a second refractive index. The first refractive index is higher than the second refractive index. Further, the channel includes a reflective material coating disposed on an inner surface or an interface of the channel.

Another exemplary embodiment of the invention is a method of using an optofluidic device. The method includes radiating monochromatic electromagnetic radiation on the optofluidic device; interacting at least a portion of the radiation with a solid, a liquid, a gas, a colloidal, or a suspension sample housed in a channel to generate photonic signals having Raman scattering and Rayleigh scattering. The sample includes a first refractive index, and where the channel is defined by a cladding region having a second refractive index, where the second refractive is higher than the first refractive index. The method further includes guiding at least a portion of the photonic signals out of the optofluidic device, and directing the photonic signals to a spectrograph to generate electrical signals proportional to one or more of a physical, a chemical, or a biological signature of the sample.

These and other advantages and features will be more readily understood from the following detailed description of preferred embodiments of the invention that is provided in connection with the accompanying drawings.

These and other advantages and features will be more readily understood from the following detailed description of preferred embodiments of the invention that is provided in connection with the accompanying drawings.

DETAILED DESCRIPTION OF EXEMPLARY EMBODIMENTS

Figure 1:
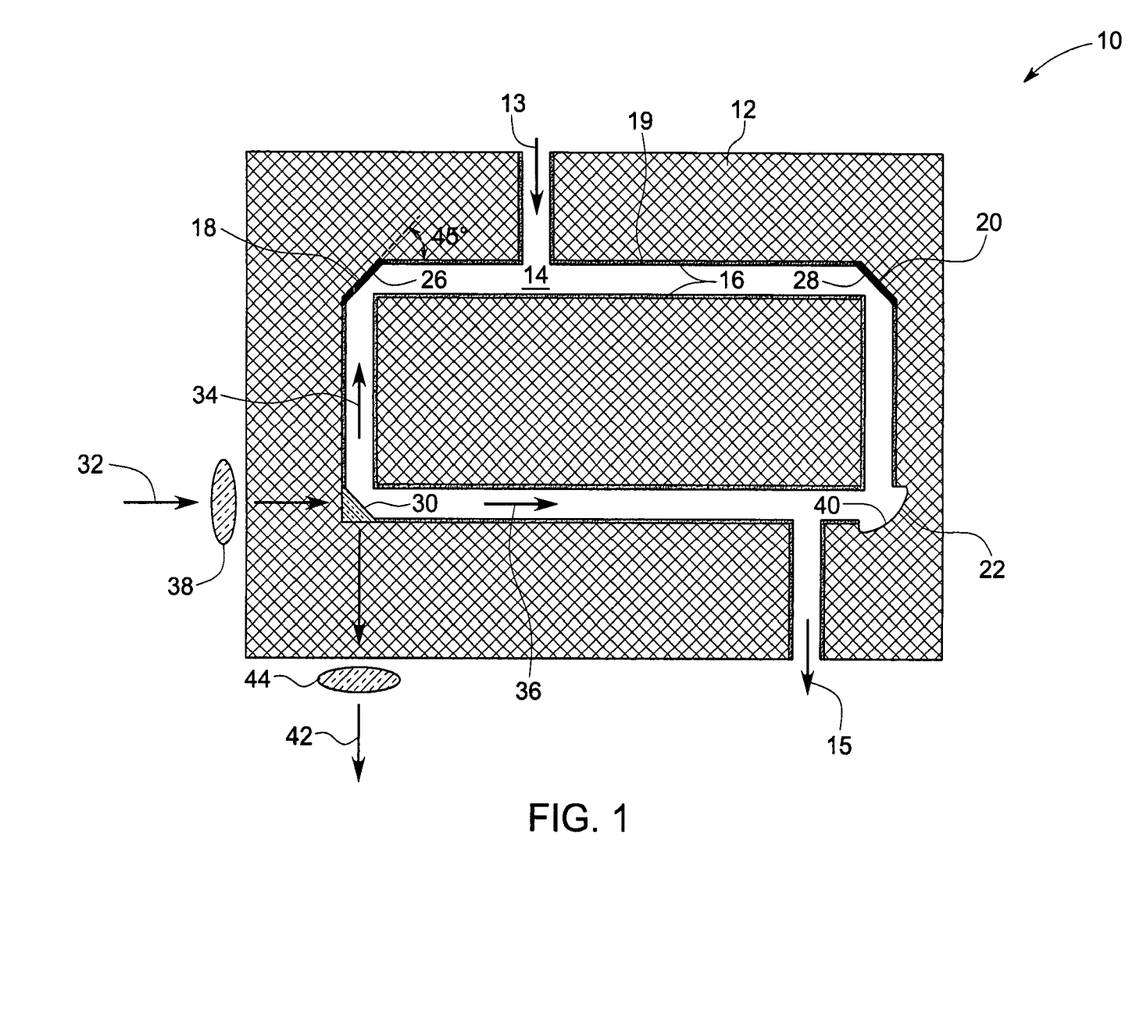
FIGS. 1-2 are cross-sectional views of optofluidic devices in accordance with exemplary embodiments of the invention.

Referring now to FIG. 1, an optofluidic device 10 having a cladding region 12 and a channel 14 is depicted. The cladding region 12 has a first refractive index. The channel 14 is defined by the cladding region 12 such that the cladding region 12 forms an inner surface or an interface 16 of the channel 14. In other words, the channel 14 is a hollow region surrounded by the cladding region 12. Further, the channel 14 is configured to house a sample (not shown), which may be one or more of a liquid, a gas, a solid, a colloidal, or a suspension. The samples may have a second refractive index. The second refractive index may be higher than the first refractive index. However, as will be described in detail below, while employing reflective material coating 19 at the inner surface or interface 16 of the channel 14, the second refractive index may be lower than the first refractive index. In this case, the light going out of the channel 14 may be reflected back into the channel 14 by the reflective material coating 19, thereby allowing the possibility of the optofluidic device 10 having a core region, i.e., the sample having a relatively lower refractive index than the cladding region 12. Non-limited examples of liquid solvents for liquid samples may include solvents, such as water, methanol. Non-limited examples of gases may include vapors or mixtures of carbon dioxide, carbon monoxide, nitrogen, or combinations thereof.

The samples in the channel 14 may be caused to interact with a monochromatic electromagnetic radiation, such as a laser, to obtain signatures corresponding to chemical, or biological species present in the sample. The radiation may also include a combination of different monochromatic radiations. In one embodiment, the wavelength of the incident radiation is in a range of from about 180 nanometers to about 1.5 micrometers.

In a typical Raman spectroscopy measurement, the sample is probed with monochromatic light (usually a laser). The sample is excited with the photon source resulting in photonic signals having elastic (Rayleigh scattering) and inelastic (Raman scattering) scattering of photons. Elastically scattered photons are at the same wavelength as the probing light and do not exchange energy with the sample molecules. These photons do not contribute to the Raman spectroscopy in identifying the signatures of various species present in the sample. However, inelastically scattered photons caused by inelastic interaction between the radiation and the sample, are either red (stokes) or blue shifted (anti stokes) and carry unique information about the identity of the material as well as its chemical and physical structure. Inelastic interaction between the photons of the electromagnetic radiation and the molecules of the sample result in the excitation of vibrational and/or rotational modes of molecular bonds. This inelastic interaction leads to energy losses for most photons and gains for some. This translates into wavelength shifts in the back-scattered photons. This inelastic scattering is known as Raman scattering and is typically a very weak signal in comparison to Rayleigh scattering (elastic scattering), which does not involve any energy exchange for the corresponding photons.

In one embodiment, the low intensity of the Raman signal is addressed by employing hollow waveguides having liquid or gaseous environments for the sample. In addition to Raman and Rayleigh scattering, in one embodiment, the photonic signals may also include fluorescence, absorption, transmission, or combinations thereof. The hollow channel 14 does not contribute to Raman scattering or fluorescence noise, which is otherwise produced in conventional channels having a solid core. In one embodiment, the signal enhancing particles are employed for achieving surface-enhancement of surface area of the inner surface.

Generally, in Teflon® based optofluidic devices, where the refractive index of the cladding is typically lower than the refractive index of the core, the core-cladding interface prevents the radiation from exiting the optofluidic device via the cladding. It should be appreciated that in Teflon® based devices, in accordance with Snell's law, the core-cladding interface allows light to be totally internally reflected within an angular range governed by the ratios of the refractive indices of the two materials. Therefore, the light may be confined inside the channel for various analytical applications. However, the optofluidic devices based on this principle limit the choices for the environment of the analyte.

However, in some applications, it may be desirable to place the analyte in a gaseous environment. In the present invention, the channel 14 may house a liquid or a gas environment for analytes by employing a reflective material coating 19 in combination with a cladding region 12, where the cladding region 12 has a higher refractive index material relative to the environment employed for the analytes. The reflective material coating 19 may be continuous throughout the inner surface 16. The cladding region 14 may include different kinds of materials in combination with the reflective material coating 19. In one embodiment, the cladding region 12 may include a semiconductor material, a liquid, a gas, a photonic crystal. In one embodiment, the semiconductor material may include silicon, silicon carbide, porous silicon, porous silicon carbide, gallium nitride, gallium arsenide, a group III compound, a group V compound, or combinations thereof. In an exemplary embodiment, the liquid of the cladding region 14 may include a three-dimensional sheath flow. As will be discussed in detail below with regard to FIG. 2, while employing a liquid or gas in the cladding region 12, a surrounding material may be employed to house the liquid or the gas of the cladding region 12 and to define the cladding region 12.

In embodiments of the invention, a reflective material coating 19 may be applied to the inner surface 16 of the channel 14. In cases where the sample, which forms the core of the optofluidic device 10, is surrounded by the cladding region 12 having a higher refractive index, the electromagnetic radiation incident on the sample may be lost by refraction. That is, the incident radiation may be lost by penetration out of the channel 14 via the cladding region. In these cases, the reflective material coating 19 may be employed. The reflective material coating 19 may reflect the outgoing radiation back into the channel 14, thereby facilitating the retention of the radiation in the channel 14. In one embodiment, the reflective material coating 19 may include gold, silver, copper, aluminum, or combinations thereof. The reflective material coating 19 may be continuous to avoid any leakage of the radiation from a portion of the optofluidic device 10. However, in one embodiment, the cladding region 12 may be tailored to have predetermined permissivity for the radiation in selected portions. For example, while employing a combination of more than one monochromatic radiation, the inner surface 16 may be tailored so as to permit a radiation of a particular wavelength to transmit out of the optofluidic device 10 via the cladding region 12, while retaining the other monochromatic radiations in the optofluidic device 10. In one embodiment, the cladding 12 forms a resonating structure with the channel 14 having a liquid or a gas sample. While employing a photonic crystal or an omni-reflector in the cladding region 12, the reflective material coating 19 may not be required to re-direct the outgoing radiation from the cladding region 12 back in the channel 14.

In some embodiments, the cladding region 12 may include a photonic crystal, or an omni-reflector, or both. As used herein, the term "photonic crystal" refers to a periodic dielectric or metallo-dielectric structure that is designed to affect the direction of propagation of electromagnetic waves (EM) in a predetermined manner. When employing a photonic crystal in the cladding region 12, the optofluidic device 10 may or may not employ the reflective material coating 19 on the inner surface 16 of the channel 14. Similarly, while employing an omni-reflector in the cladding region 12, the reflective material coating 19 may not be employed because the omni-reflector may itself be configured to reflect the radiation back into the channel 14.

The channel 14 includes an inlet 13 for the sample to enter the channel 14. The channel 14 has an outlet 15 for taking out the sample once it has reacted with the radiation.

The channel 14 may be in the shape of a straight tube. Alternatively, as illustrated, the channel 14 may include one or more bends 18, 20, 22 and 24. One or more of these bends in the channel 14 may include mirrors to direct the light along the channel 14. For example, the bends 18 and 20 may include mirrors 26 and 28. In one embodiment, the mirrors 26 and 28 may be disposed at an angle of about 45° with the inner surface 16 of the channel 14. In one embodiment, the mirrors 26 and 28 may be semi-transparent mirrors. In the channels having the bends 18, 20, 22 and 24, the incident radiation intended to interact with the samples housed inside the channel 14, may circulate through the channel 14 as opposed to straight channels (without bends) where the light comes across the sample only once while traveling through the channel 14. Accordingly, the channel 14 having the bends may result in improved sampling efficiency for a particular amount of sample because the amount of sample needed for the analysis may reduce as the interaction between the radiation and the sample increases. The inner surface 16 of the channel 14 may be modified by attaching a plurality of signal enhancing particles disposed thereon. For example, for biological assays, it may be desirable to modify the surface 16 of the channel 14 for optimal fluorescence detection and for adhesion of biological cells to the surface of the channel 14.

The optofluidic device 10 may further include a beam splitter 30. The beam splitter 30 may be an optical lens that is configured to split a beam 32 of laser pumped into the channel 14, the split beam then traveling in two directions is represented by arrows 34 and 36. Further, the beam 32 may be focused by using a micro-lens 38. Once the beam has circulated through the channel 14, the beam 32 may exit the channel 14 as represented by arrow 42. While exiting, the beam 32 may be focused or collimated by using a micro-lens 44.

The optofluidic device 10 may further include a corner reflector 40 positioned at the bend 22. The corner reflector 40 may be employed to re-condition the light. For example, the corner-reflector 40 may facilitate beam shaping, collimating of the radiation in the channel 14. Additionally, a micro-pump may be employed to pump the sample solution in the channel 14, a micro-valve may be employed to control the flow of the sample solution in the channel 14, and a sample mixer may be employed to mix the sample in the channel 14. Such peripherals may be integrated to the optofluidic device 10 to complete the optofluidic circuit. In one embodiment, the radiation may be collimated into a beam 32 at the inlet 13 of the channel 14. For example, the radiation may be launched axially into the channel 14 by inserting an optical fiber, coupled to a light source, into one end of the optofluidic device 10.

In one embodiment, the optofluidic device 10 may be configured to perform light absorption and fluorescence measurements for analytes in liquid or gas phase solution in conjunction with other devices, such as spectrometer. Such detections facilitate determining chemical, biological properties of small amounts of analytes in a sample solution.

Figure 2:
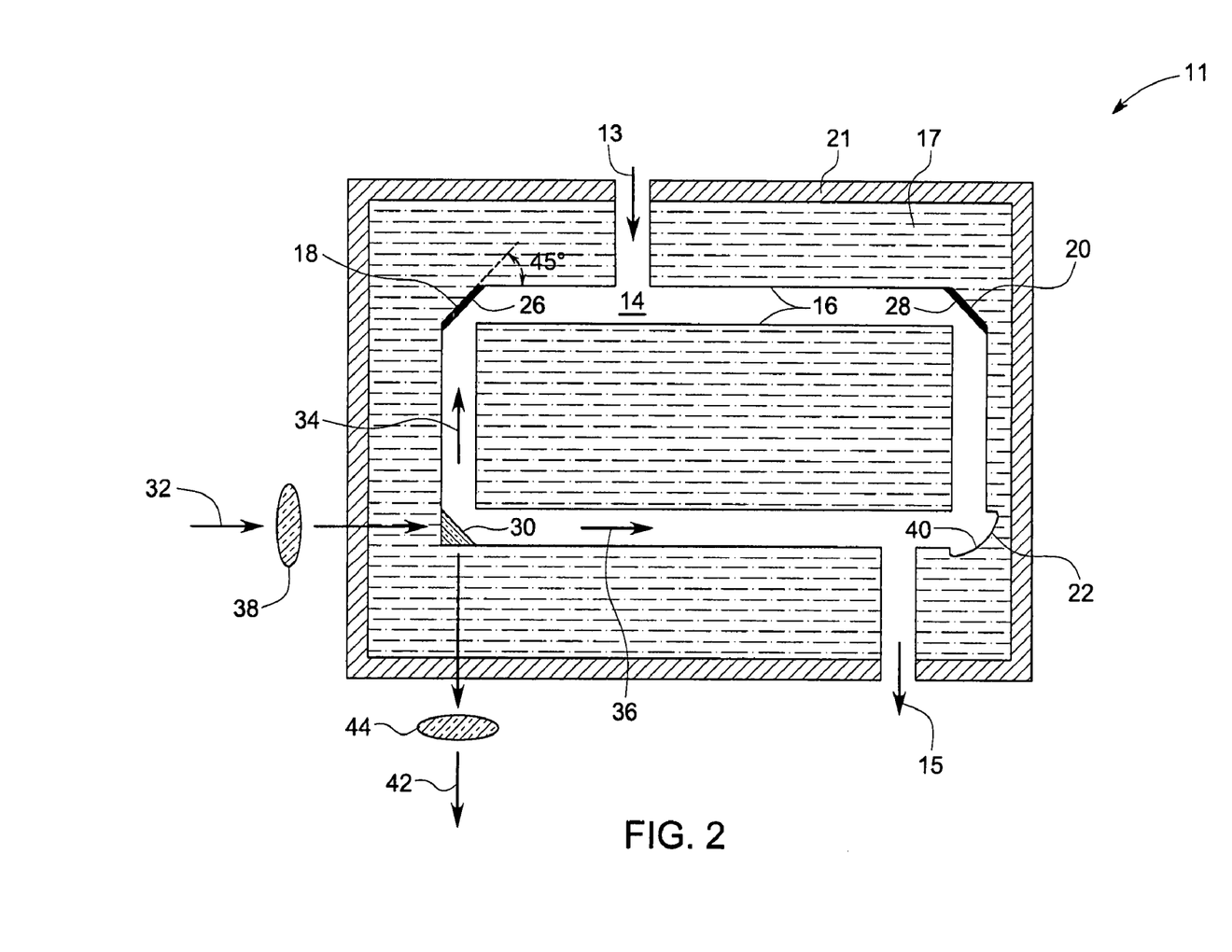

FIG. 2 illustrates an alternate embodiment of the optofluidic device 10 of FIG. 1. In the illustrated embodiment, the optofluidic device 11 includes a liquid. For example, the liquid may include a three-dimensional (3D) laminar sheath flow 17 to form the cladding region. Additionally, a surrounding material 21 may be employed to house the sheath flow 17 and to define the cladding region. In one embodiment, the refractive index of the liquid of the sheath flow 17 may be less than the refractive index of the sample in the channel 14. In one embodiment, a gas flow may be introduced in place of the laminar liquid sheath flow 17 to form the cladding region.

Figure 3:
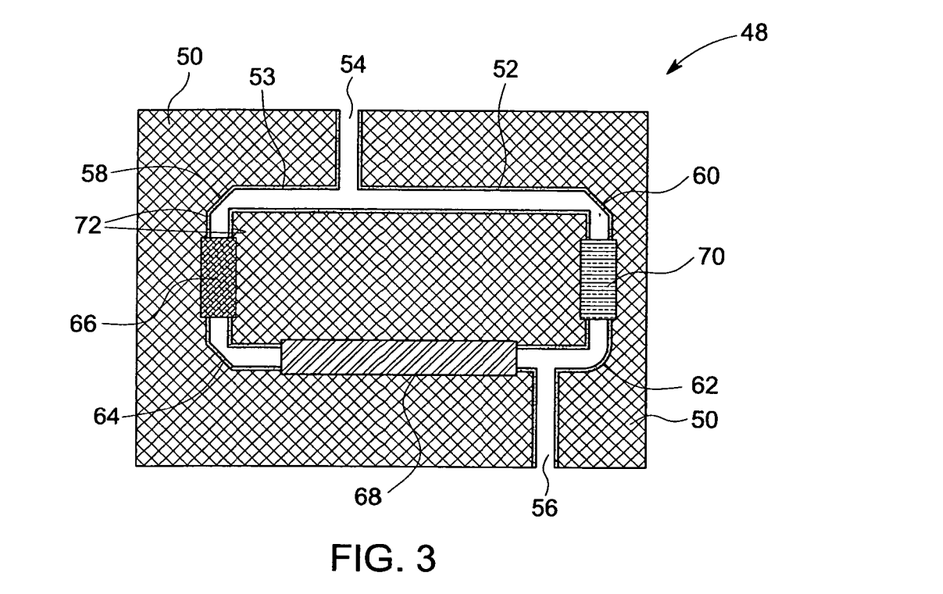
FIGS. 3-4 are cross-sectional views of optofluidic devices employing a plurality of signal enhancing particles attached to antibodies or other analyte capture molecules disposed on the inner surface of the channel in accordance with exemplary embodiments of the invention.

Referring now to FIG. 3, an optofluidic device 48 having a cladding region 50, a channel 52, a reflective material coating 53, an inlet 54 and an outlet 56 is illustrated. Although not illustrated, the optofluidic device 48 may include mirrors and/or beam splitters or corner reflectors disposed on bends 58, 60, 62 or 64. The channel 52 includes three different antibodies or other analyte capture molecules 66, 68 and 70 disposed in three different locations of the inner surface 72 of the channel 52. A plurality of signal enhancing particles may be attached to the antibodies 66, 68 and 70 in the channel 52.

The plurality of signal enhancing particles may include nanoparticles, a high refractive index material, surface enhanced Raman scattering (SERS) tags, organic fluorophores, dyes, quantum dots, or combinations thereof. In one embodiment, the nanoparticles may include gold or silver. In one embodiment, gold or silver nanoparticles may be employed as a base for detection tags such as SERS tags. Additionally, gold or silver nanoparticles may also be employed for surface enhancement for Raman scattering. Detection tags may be employed in biological assays to identify a particular product or event from among the variety of molecules and events present in a cell or biological extract. The tags may be used to display many different spectra, thus these tags may be used for multiplexed detection schemes. The tags generate a large number of photons, which may be readily detected. The spectra acquired from mixtures of these tags may be analyzed to give accurate amounts of the analytes present in the solution.

In one embodiment, the optofluidic device 48 may include two or more different types of signal enhancing particles to detect different kinds of analytes. The different types of signal enhancing particles may be located in separate locations of the optofluidic device 48 to enable detection of a particular analyte at a particular location. As noted above, depending on the analytes to be detected, the radiation may be either monochromatic, or may include a combination of multiple monochromatic radiations. For example, while detecting a particular analyte a monochromatic radiation may be used. To detect a group of analytes a combination of multiple monochromatic radiations may be required.

In the illustrated embodiment of FIG. 3, the output signal may be a combination of the different signatures from the tags attached to the particles, which in turn are coupled to the antibodies 66, 68 and 70. This combination of signatures may then be compared with standard signatures to detect analytes present in the sample.

Figure 4:
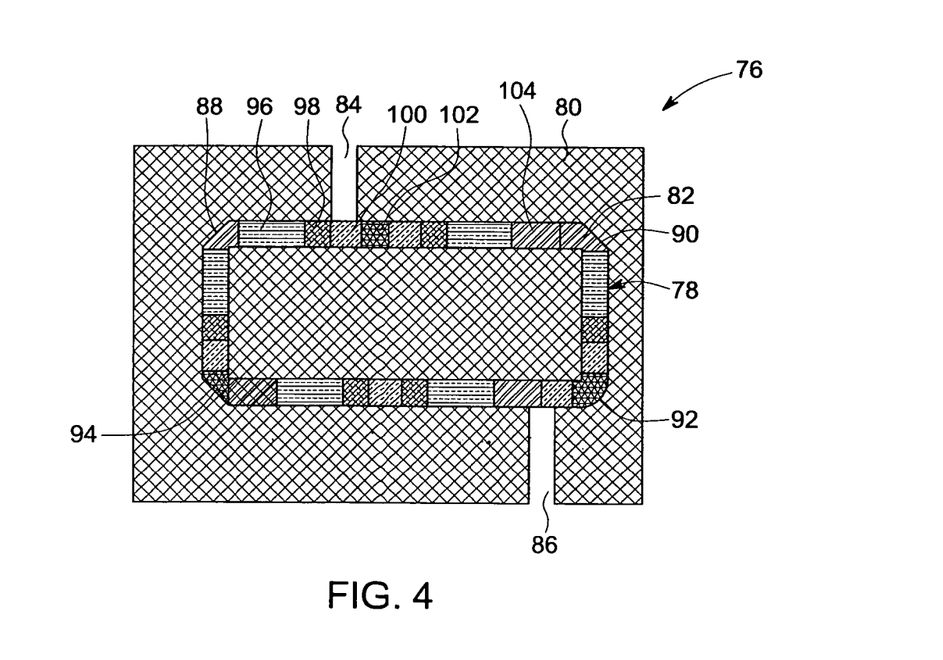

FIG. 4 illustrates an optofluidic device 76 having a patterned structure 78 employing different kinds of antibodies arranged in a periodic fashion. In the illustrated embodiment, the optofluidic device 76 includes a cladding region 80 and a channel 82 having an inlet 84 and an outlet 86. The channel 82 includes four bends 88, 90, 92 and 94. The antibodies 96, 98, 100, 102 and 104 may be periodically arranged and may be configured to detect different kinds of species.

Figure 5:
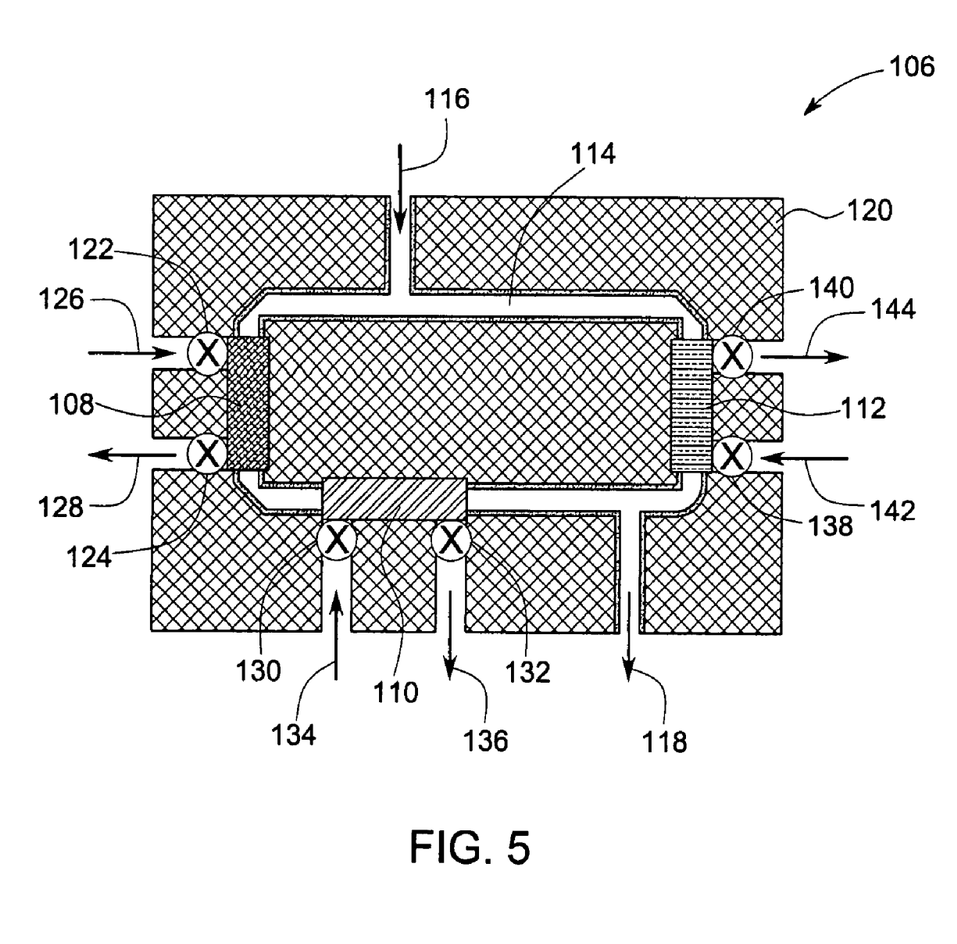
FIG. 5 is a cross-sectional view of an optofluidic device employing a patterned array of a plurality of signal enhancing particles attached to antibodies or other analyte capture molecules in accordance with an exemplary embodiment of the invention.

Turning now to FIG. 5, an optofluidic device 106 having a dynamic distribution of antibodies 108, 110 and 112 is depicted. In the illustrated exemplary embodiment, the antibodies 108, 110 and 112 are disposed in the three different locations of the channel 114 having an inlet 116 and an outlet 118 for the sample solution having the analytes. It should be appreciated that the antibodies 108, 110 and 112 may be disposed at less or more number of locations than illustrated. The optofluidic device 106 further includes a cladding region 120 disposed around and defining the channel 114. The channel 114 further includes separate inlets and outlets for the three antibodies 108, 110 and 112. The flow of the antibody 108 may be controlled by the valves 122 and 124 disposed on the inlet 126 and the outlet 128. The antibody 108 may be pumped in or pumped out through the inlet 126 and the outlet 128. Alternatively, the antibody 108 may be replaced by another antibody through these inlets and outlets. This application may be used while analyzing different analytes over a period of time. The flow of the antibody 110 may be controlled by the valves 130 and 132 for inlet 134 and outlet 136. The flow of the antibody 112 may be controlled by the valves 138 and 140 for inlet 142 and outlet 144.

In operating, the sample solution and the tags, such as SERS tags, may be pumped into the channel 114 of the device 106. The analyte particles may be attracted by the antibodies 108, 110 and 112. Subsequently, the tags may attach to the analyte particles, thereby detecting the analytes.

Figure 6:
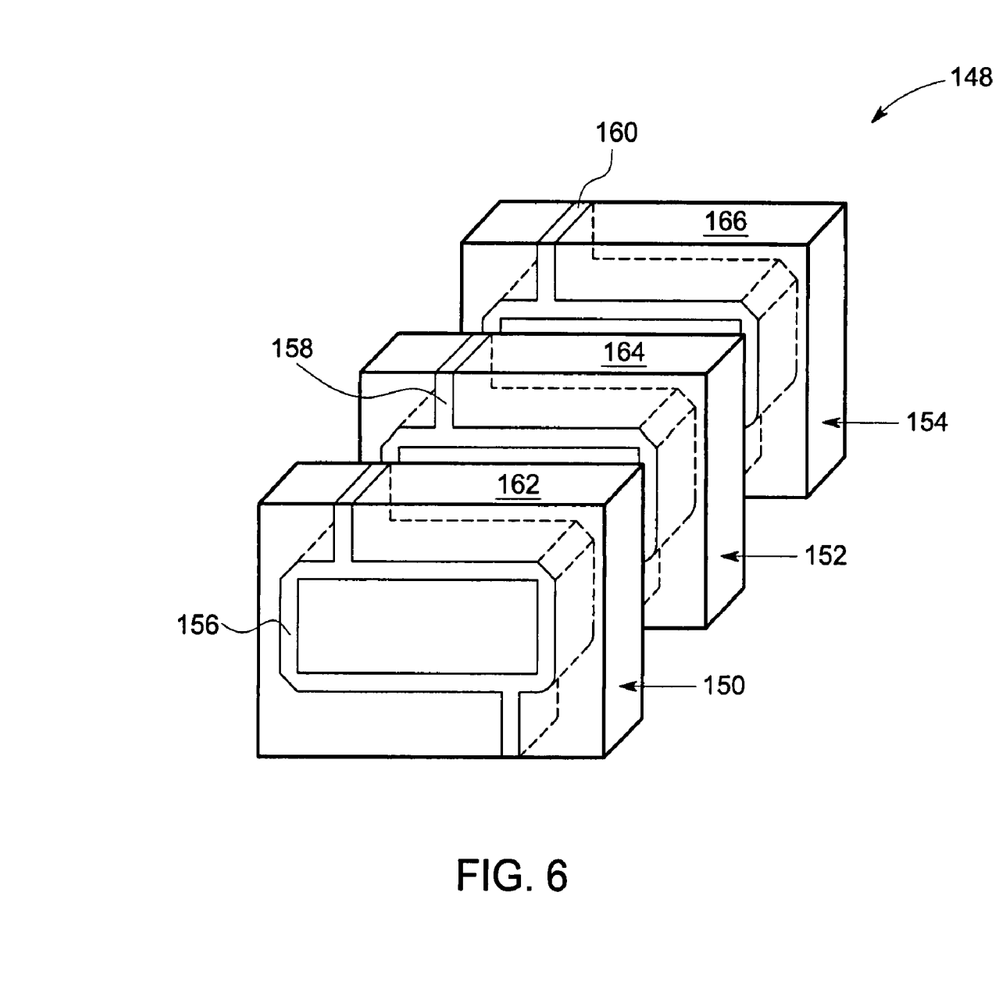
FIG. 6 is a perspective view of an optofluidic system employing a plurality of optofluidic devices in a stacked arrangement in accordance with an exemplary embodiment of the invention.

Turning now to FIG. 6, a multiplex optofluidic system 148 of the optofluidic devices 150, 152 and 154 is illustrated. In the illustrated embodiment, the optofluidic devices 150, 152 and 154 are stacked. Further, these optofluidic devices 150, 152 and 154 may be interconnected to the adjacent device. For example, the channel 156 of the device 150 may be interconnected with the channel 158 of the device 152, which in turn may be connected to the channel 160 of the device 154, by vias (not shown) extending through the thickness of the cladding regions 162, 164 and 166. In the multiplex optofluidic system 148, each of the devices 150, 152 and 154 may be configured to detect a different sample. For example, a multiple laser wavelength source may be employed to direct a particular wavelength of laser in the channel of a particular device. Further, the three channels 156, 158 and 160 may have different antibodies disposed therein and may be configured to flow in and flow out different detection tags, such as SERS tags. Accordingly, when the sample solution is flown in the three channels 156, 158 and 160, each channel may identify separate specie present in the sample solution different from the ones detected by other two channels.

Figure 7:
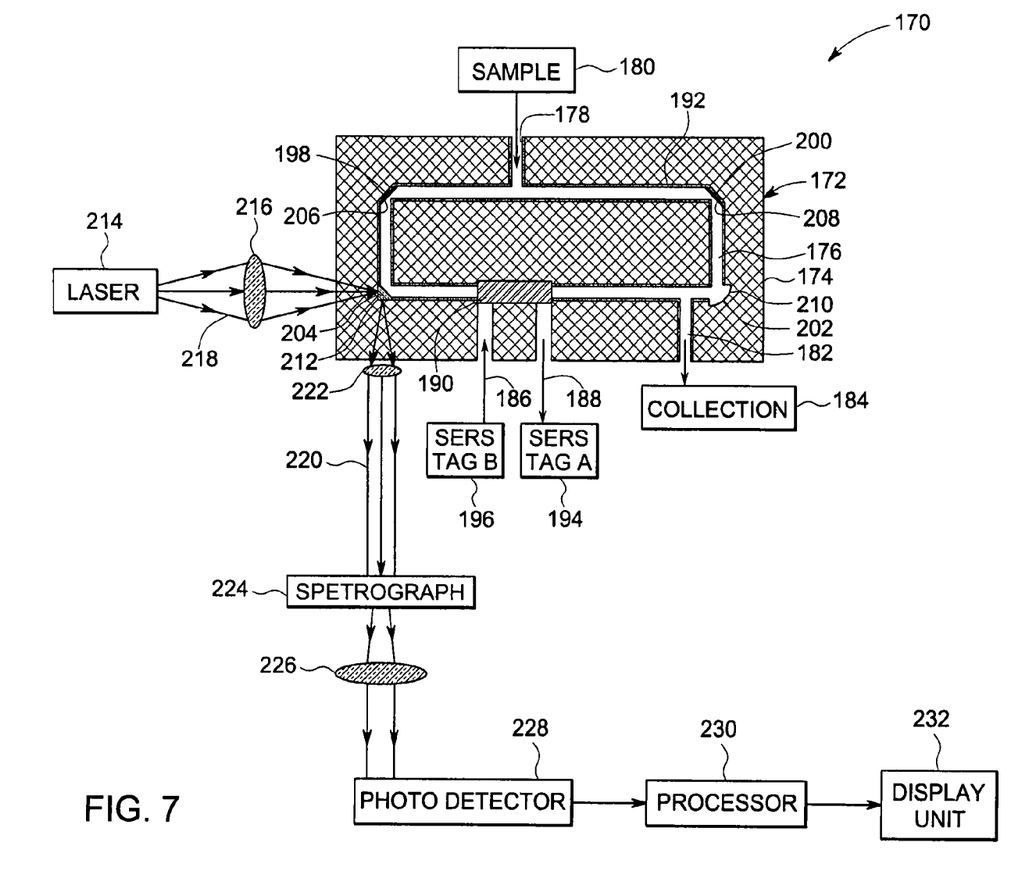
FIG. 7 is a perspective view of a system employing an optofluidic device in accordance with another exemplary embodiment of the present invention.

FIG. 7 illustrates a system 170 employing an optofluidic device 172 having a cladding region 174 and a channel 176 defined by the cladding region. The channel 176 includes inlet 178 for the sample solution 180. The channel further includes an outlet 182 for collecting the sample as represented by the block 184, after the sample has interacted with the laser. The channel 176 further includes a reflective material coating 192 disposed on the inner surface of the channel 176. Additionally, the channel 176 includes an inlet 186 and an outlet 188 for introducing antibodies or detection tags 190, such as SERS tags, in the channel 176. The antibodies or the tags 190 may be changed during the operation of the device 172. For example SERS tag A 194 may be introduced in the channel 176 for the initial time period of $T_1$ of the operation of the device. Subsequently, the SERS tag A 194 may be replaced by a different SERS tag B 196. The SERS tag B 196 may then remain in the channel 176 for a predetermined time period $T_2$. This way, different analytes may be detected by the system at different periods of time.

The channel 176 includes bends 198, 200, 202 and 204. Further, the channel 176 includes semi-reflective mirrors 206 and 208, a corner reflector 210 and a beam splitter 212. A laser source represented by the block 214 may be optically coupled with an optical lens 216 such that the radiation 218 from the laser is focused and directed to the channel 176. Once inside the channel, the radiation 218 travels through the channel 176 and interacts with the analytes in the sample solution. The radiation 220 then comes out of the channel 176. This radiation 220 is then collimated by employing an optical lens 222. The radiation 220 is then broken down to its spectral components and filtered to separate out the strong Rayleigh spectra from the Raman spectra by using the spectrograph 224. This filtration may be achieved by employing a micro electro mechanical systems (MEMS) spectrograph, such as Fabry Perot cavity. The radiation 220 may then be focused using an optical lens 226. The intensity of each of the spectral components may then be detected by employing a photodetector 228, which turn these components into electrical signals. The electrical signals are then processed by the processor 230 and displayed by a display unit 232, such as a monitor.

In one embodiment, the optofluidic device 172 may be coupled to other devices by using optical fibers. For example, for analytical applications, the optofluidic device may be coupled to the spectrometer via optical fibers. Also, the radiation, such as radiation 218 may be guided into the channel 176 by optical fibers.

These optofluidic devices may be used in applications such as liquid chromatography detection, stopped-flow detection, drinking water analysis, as well as in environmental and oceanographic monitoring systems. For example, the optofluidic devices of the present invention may be employed in healthcare applications, water technology, sensing applications, or security applications. For example, in healthcare applications, the optofluidic devices may be employed to monitor blood analytes of a patient undergoing intra-vascular drug delivery, narcotics disposal, or anesthetic gas monitoring. In water technology applications, the optofluidic devices may be used for fouling detection of the membranes, or water quality monitoring. In sensing applications, the optofluidic devices may be used for detecting uniformity of the blend, or online monitoring of chemical species. In security applications, the optofluidic devices may be used for detection of chemical or biological species, or detection of narcotics or explosives detection.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. For example, while the optofluidic device is described in conjunction with detection techniques, it should be appreciated that the optofluidic device may find utility for any application in which a waveguide may be employed. Additionally, while various embodiments of the invention have been described, it is to be understood that aspects of the invention may include some of the described embodiments. Accordingly, the invention is not to be seen as limited by the foregoing description, but is only limited by the scope of the appended claims.

What is claimed as new and desired to be protected by Letters Patent of the United States is:

1. A non-resonant optofluidic device, comprising:
    a cladding region having a first refractive index; and
    a channel defined by said cladding region, wherein said channel is configured to house one or more of a liquid, a gas, a solid, a colloidal, or a suspension sample containing an analyte and having a second refractive index higher than said first refractive index, and wherein said channel is configured to interact with monochromatic electromagnetic radiation to generate photonic signals having Raman scattering and Rayleigh scattering and to guide at least a portion of the photonic signals out of the non-resonant optofluidic device.

2. The optofluidic device of claim 1, further comprising a reflective material coating disposed on an inner surface or an interface of said channel.

3. The optofluidic device of claim 1, wherein said cladding region comprises a liquid, a gas, a semiconductor material, a photonic crystal, an omni-reflector, or combinations thereof.

4. The optofluidic device of claim 3, wherein said liquid comprises a three-dimensional sheath flow.

5. The optofluidic device of claim 4, further comprising a surrounding material defining said cladding region.

6. The optofluidic device of claim 3, wherein said semiconductor material comprises silicon, silicon carbide, porous silicon, porous silicon carbide, gallium nitride, gallium arsenide, a group III compound, a group V compound, or combinations thereof.

7. The optofluidic device of claim 1, further comprising a plurality of signal enhancing particles disposed on said inner surface of said channel.

8. The optofluidic device of claim 7, wherein each said plurality of signal enhancing particles is attached to an antibody.

9. The optofluidic device of claim 7, wherein said plurality of signal enhancing particles comprises nanoparticles, a high refractive index material, surface enhanced Raman scattering tags, organic fluorophores, dyes, quantum dots, or combinations thereof.

10. The optofluidic device of claim 7, wherein said plurality of signal enhancing particles comprise two or more different types of particles, wherein each of said two or more different types of particles is located in separate locations.

11. The optofluidic device of claim 1, wherein said channel has at least one bend, wherein said at least one bend comprises a beam splitter disposed at said bend.

12. The optofluidic device of claim 1, wherein said radiation comprises multiple monochromatic radiation.

13. The optofluidic device of claim 12, wherein a portion of said cladding region is permissive to selective wavelengths in said multiple monochromatic radiation.

14. The optofluidic device of claim 1, wherein said cladding region along with said channel having said sample forms a resonate structure to confine said radiation in said optofluidic device.

15. The optofluidic device of claim 1, wherein said optofluidic device comprises an optical waveguide.

16. The non-resonant optofluidic device of claim 1, wherein the photonic signals are directed to a spectrograph to generate electrical signals proportional to one or more of a physical, a chemical, or a biological signature of the sample.

17. A non-resonant optofluidic device, comprising:
a cladding region having a first refractive index; and a channel defined by said cladding region, wherein said channel is configured to house one or more of a liquid, a gas, a solid, a colloidal, or a suspension sample having a second refractive index lower than said first refractive index, and wherein said channel is configured to interact with monochromatic electromagnetic radiation to generate photonic signals having Raman scattering and Rayleigh scattering and to guide at least a portion of the photonic signals out of the non-resonant optofluidic device, wherein said channel has at least one bend and a beam splitter disposed at said bend; and
a reflective material coating disposed on an inner surface or an interface of said channel.

18. An optofluidic system, comprising:
a non-resonant optofluidic device having an optical interaction path between a radiation and one or more of a liquid, a gas, a solid, a colloidal, or a suspension sample containing an analyte, said device comprising:
a first region having a first refractive index; and
a second region having a second refractive index higher than said first refractive index configured to dispose said sample therein and to interact with monochromatic electromagnetic radiation to generate photonic signals having Raman scattering and Rayleigh scattering and to guide at least a portion of the photonic signals out of the non-resonant optofluidic device, said first refractive index region surrounding said second refractive index region to define a space for interaction between said radiation and said sample.

19. The optofluidic system of claim 18, further comprising a reflective material coating disposed on an inner surface or an interface of said second refractive index region.

20. The optofluidic system of claim 18, further comprising a spectrometer optically coupled to said optofluidic device.

21. The optofluidic system of claim 18, further comprising disposing a fiber at a first end of said first refractive index region to direct said beam inside said channel.

22. The optofluidic system of claim 18, further comprising disposing a fiber at a second end of said first refractive index region to direct said beam out of said channel.

23. The optofluidic system of claim 18, comprising a plurality of optofluidic devices, wherein at least two of said plurality of optofluidic devices, wherein said at least two optofluidic devices are interconnected.

24. The non-resonant optofluidic device of claim 18, wherein the photonic signals are directed to a spectrograph to generate electrical signals proportional to one or more of a physical, a chemical, or a biological signature of the sample.

25. A method of using a non-resonant optofluidic device, comprising:
radiating monochromatic electromagnetic radiation on the optofluidic device;
interacting at least a portion of the monochromatic electromagnetic radiation with one or more of a liquid, a solid, a gas, a colloidal, or a suspension sample containing an analyte and being housed in a channel to generate photonic signals having Raman scattering and Rayleigh scattering, wherein the sample comprises a first refractive index, and wherein the channel is defined by a cladding region having a second refractive index lower than the first refractive index;
guiding at least a portion of the photonic signals out of the optofluidic device; and
directing the photonic signals to a spectrograph to generate electrical signals proportional to one or more of a physical, a chemical, or a biological signature of the sample.

26. The method of claim 25, further comprising filtering the photonic signals to at least partially separate out the Rayleigh scattering from the Raman scattering.

* * * * *

UNITED STATES PATENT AND TRADEMARK OFFICE
CERTIFICATE OF CORRECTION

PATENT NO. : 7,574,089 B1 Page 1 of 1
APPLICATION NO. : 11/400947
DATED : August 11, 2009
INVENTOR(S) : Zribi et al.

It is certified that error appears in the above-identified patent and that said Letters Patent is hereby corrected as shown below:

In Fig. 7, Sheet 6 of 6, for Tag "224", Line 1, delete "SPETROGRAPH" and insert -- SPECTROGRAPH --, therefor.

In Column 1, Line 17, delete "retains" and insert -- retained --, therefor.

Signed and Sealed this

Twenty-seventh Day of October, 2009

David J. Kappos
*Director of the United States Patent and Trademark Office*